US008535683B2

(12) United States Patent
Kersten et al.

(10) Patent No.: US 8,535,683 B2
(45) Date of Patent: *Sep. 17, 2013

(54) INTRANASAL OR INHALATIONAL ADMINISTRATION OF VIROSOMES

(75) Inventors: Alexander J. Kersten, Weesp (NL); Lisya Gerez, Weesp (NL); Pieter J. Schoen, Weesp (NL); Jozef J. P. Nauta, Weesp (NL); Dorine H. van Rheineck Leyssius, Weesp (NL)

(73) Assignee: Abbott Biologicals B.V., Weesp (NL)

( * ) Notice: Subject to any disclaimer, the term of this patent is extended or adjusted under 35 U.S.C. 154(b) by 0 days.

This patent is subject to a terminal disclaimer.

(21) Appl. No.: 11/723,672

(22) Filed: Mar. 21, 2007

(65) Prior Publication Data

US 2007/0224220 A1    Sep. 27, 2007

Related U.S. Application Data

(60) Provisional application No. 60/784,462, filed on Mar. 22, 2006.

(51) Int. Cl.
*A61K 39/12* (2006.01)
*A61K 39/145* (2006.01)
*C12Q 1/70* (2006.01)

(52) U.S. Cl.
USPC .................. 424/206.1; 424/209.1; 435/5

(58) Field of Classification Search
None
See application file for complete search history.

(56) References Cited

U.S. PATENT DOCUMENTS

| 5,437,267 A | 8/1995 | Weinstein et al. |
| 2001/0053368 A1* | 12/2001 | Burt et al. .................. 424/206.1 |
| 2003/0180351 A1* | 9/2003 | Gluck et al. .................. 424/450 |
| 2008/0038294 A1 | 2/2008 | Kersten et al. |

FOREIGN PATENT DOCUMENTS

| JP | 6-503555 | | 4/1994 |
| WO | WO 88/08718 | | 11/1988 |
| WO | WO 92/03162 | | 3/1992 |
| WO | WO 01/21151 A1 | | 3/2001 |
| WO | WO 01/21152 A1 | | 3/2001 |
| WO | WO 01/21207 A2 | | 3/2001 |
| WO | WO-2004-071492 | * | 8/2004 |
| WO | WO 2004/110486 A1 | | 12/2004 |

OTHER PUBLICATIONS

Gluck et al., Influenza virosomes as an efficient system for adjuvanted vaccine delivery, 2004, Expert Opinion in Biological Therapy, vol. 4, No. 7, pp. 1139-1145.*
Huckriede et al., The virosomes concept for influenza vaccines, 2005, Vaccine, Supplement 1, pp. 26-38.*
Nelson and Cox, Principles of Biochemistry, 2005, W.H. Freeman and Company, 4$^{th}$ Ed., G-9 and G-11.*
Glück, et al., "Phase 1 Evaluation of Intranasal Virosomal Influenza Vaccine with and without *Escherichia coli* Heat-Labile Toxin in Adult Volunteers", Journal of Virology, vol. 73, No. 9, pp. 7780-7786, (Sep. 1999).
Durrer, et al., "Mucosal antibody response induced with a nasal virosome-based influenza vaccine", Vaccine, Butterworth Scientific, Guildford, GB, vol. 21, No. 27-28, pp. 4328-4334, (Oct. 1, 2003).
Mutsch, M. et al., "Use of the Inactivated 1-33 Intranasal Influenza Vaccine and the Risk of Bell's Palsy in Switzerland", N Engl J Med, vol. 350, No. 9, pp. 896-903, (Feb. 26, 2004).
Couch R.B., "Nasal Vaccination, *Escherichia coli* Enterotoxin, and Bell's Palsy", N Engl J Med, vol. 350, No. 9, pp. 860-861, (Feb. 26, 2004).
Stegmann et al., "Functional reconstitution of influenza virus envelopes," The EMBO Journal, vol. 6, No. 9, pp. 2651-2659, 1987.
Gluck et al., "Immunogenicity of new virosome influenza vaccine in elderly people," Lancet, vol. 344, No. 8916, pp. 160-163, 1994.
Daubeney, P., Taylor, C.J., McGaw, J., Brown, E.M., Ghosal, S., Keeton, B.R., Palache, B., Kerstens, R. Immunogenicity and tolerability of a trivalent influenza subunit vaccine (Influvac$^R$) in high-risk children aged 6 months to 4 years. BJCP Mar. 1997, 51(2): 87-90.
Glück R, Burri KG, Metcalfe I. Adjuvant and antigen delivery properties of virosomes. Curr. Drug Deliv. 2005 2:395-400.
Glück R, Mischler R, Durrer P, Furer E, Lang a, Herzog c, Cryz SI. Safety and Immunogenicity of Intranasally Administered Inactivated Trivalent Virosome-Formulated Influenza vaccine Containing *Escherichia coli* Heat-Labile Toxin as a Mucosal Adjuvant. J Infect Dis. 2000 181:1129-32.
Huckriede A, Bungener L, Stegmann T, Daemen T, Medema J, Palache AM, Wilschut J. The virosome concept for influenza vaccines. Vaccine 2005 23(Suppl 1):S26-38.
Keitel W, Piedra PA. Live cold-adapted, reassortant in influenza vaccines (USA). In: Textbook of Influenza. Nicholson KG, Webster RG, Hay AJ (Ed), Blackwell Science Oxford, UK, 373-390 (1998).
Kuper CF, Koornstra PJ, Hameleers DM, Biewenga J, Spit BJ, Duijvestein AM, van Breda Vriesman PJ, Sminia T. The role of nasopharyngeal lymphoid tissue. Immunol. Today 1992 13:219-24.
Maassab HF, Bryant ML. The development of live attenuated cold-adapted influenza virus vaccine for humans. Rev.Med.Virol. Oct.-Dec. 1999;9(4):237-44.
Maassab HF. Adaptation and growth characteristics of influenza virus at 25°C, Nature 213, 612-14 (1967).
Note for Guidance on Harmonisation of Requirements for Influenza Vaccines. EMEA/CpMP/BWP/214/96, Mar. 12, 1997.
Read R.C.,Naylor S.C.,Potter C.W.,Bond J.,Jabbal-Gill I.,Fisher A.,Illum L.,Jennings R. Effective nasal influenza vaccine delivery using chitosan. Vaccine 2005;23(35):4367-74.
Samdal HH, Bakke H, Oftung F, Holst J, Haugen IL, Korsvold GE, Kristoffersen AC, Krogh G, Nord K, Rappuoli R, Berstad AKH, Haneberg B. Anon-Living Nasal Influenza Vaccine Can Induce Major Humoral and Cellular Immune Responses in Humans without the Need for Adjuvants. Human Vaccines 1:2, 85-90; Mar./Apr. 2005.

(Continued)

*Primary Examiner* — Benjamin P Blumel
(74) *Attorney, Agent, or Firm* — Finnegan, Henderson, Farabow, Garrett & Dunner L.L.P.

(57) ABSTRACT

Compositions comprising influenza virosomes comprising reconstituted envelopes of one or more influenza strains are used in vaccine formulations, including intranasal or inhalation formulations, to induce an immune response against one or more influenza strains. The virosomes of the composition are derived entirely from influenza viral particles and comprise the influenza antigen haemagglutinin. No lipid from an external source is added to the virosomes. In addition, no separate adjuvant or immune stimulator is added to the composition.

16 Claims, No Drawings

(56) References Cited

OTHER PUBLICATIONS

Treanor J, Nolan C, O'Brien D, Burt D, Lowell G, Linden J, Fries L. Intranasal administration of a proteosome-influenza vaccine is well-tolerated and induces serum and nasal secretion influenza antibodies in healthy human subjects. Vaccine 2006;24(3):254-62.

Zuercher AW, Coffin SE, Thurnheer MC, Fundova P, Cebra JJ. Nasal-associated lymphoid tissue is a mucosal inductive site for virus-specific humoral and cellular immune responses. J. Immunol. 2002 168:1796-803.

Bron et al., "[23] Preparation, Properties, and Applications of Reconstituted Influenza Virus Envelopes (Virosomes)," Methods in Enzymology, 220: 313-331 (1993).

Metsikko et al., "Reconstitution of the fusogenic activity of vesicular stomatitis virus" EMBO J. 5(13):3429-35 (1986).
Specification and pending claims of copending U.S. Appl. No. 11/723,452, filed Mar. 20, 2007.
Goodwin et al., "Antibody response to influenza vaccination in the elderly: A quantitative review", Vaccine, 24 2006, pp. 1159-1169/.
Palache et al., "Antibody response after influenza immunization with various vaccine doses: a double-blind, placebo-controlled, multi-centre, dose-response study in elderly nursing-home residents and young volunteers" Vaccine, vol. 11, Issue 1, 1993, pp. 3-9.
Clark A.R., "Medical Aerosol Inhalers: Past, Present, and Future", Aerosol Science and Technology, 22(4), 1995, pp. 374-391.

* cited by examiner

INTRANASAL OR INHALATIONAL ADMINISTRATION OF VIROSOMES

This application claims the benefit of U.S. Provisional Application No. 60/784,462, filed Mar. 22, 2006, the disclosure of which is incorporated by reference in its entirety.

FIELD OF THE INVENTION

The present invention relates, for example, to compositions for inactivated influenza vaccines and routes of administration wherein a single intranasal or inhalational administration yields a systemic immune response that is positively correlated to clinical protection.

BACKGROUND OF THE INVENTION

Various concepts for immunization against influenza via the nasal or oropharyngeal route and using inactivated influenza antigen have been explored as needle-less alternatives to the subcutaneous or intramuscular immunization. Experimental data supportive for needle-less approaches have been generated in animal models. Concepts using inactivated influenza antigen (such as chemically inactivated whole virus particles, or further processed viral components such as split virus, or purified surface antigens haemagglutinin (HA) and/or neuraminidase (NA)) for immunization via the intranasal route that are supported by animal data include either the use of an adjuvant or immune stimulator in combination with the inactivated influenza antigen, or require multiple vaccination. An adjuvant is any substance that enhances the immunogenicity of antigens mixed with it. In humans successful vaccination against influenza via the intranasal route has only been reported for (a) live (cold adapted strains) influenza vaccines (FluMist™, MedImmune Vaccines Inc) (Refs 1, 2, 3), (b) virosomal influenza vaccine adjuvanted with the heat labile toxin of *E. coli* (NasalFlu, Berna Biotech Ltd). (Ref 4) or (c) using high amounts of antigen and repeated vaccination (Refs 5, 10, 11). Although live vaccines are capable of inducing a satisfactory immune response, their specific nature of being a live virus causes additional safety concerns, and is likely to induce side effects due to the required viral replication round in the upper respiratory tract. Also the required storage conditions are limiting the commercialization of these products. A strong association between the use of the intranasal influenza vaccine with *E. coli* HLT as adjuvant, and facial paralysis (Bell's Palsy), led to withdrawal of the HLT adjuvanted virosomal vaccine from the market (Ref 6).

The efficacy of influenza vaccines in a given population may be estimated by assessing immunogenicity parameters relating to the amount of anti-influenza antibodies that are generated after vaccination. These immunogenicity parameters, generally referred to as CHMP criteria, are used for the annual re-licensing of inactivated influenza vaccines. (Ref 7). To date, successful immunization of humans against influenza, meeting these immunology requirements or CHMP criteria (Ref 7), with one single intranasal administration of an inactivated vaccine, and without the addition of an adjuvant, being an additional ingredient of the vaccine that is not derived from the infective agent that the vaccine is intended to prevent for and that is added to the vaccine formulation for the purpose of enhancing the immune response to the antigen, has not been described. It is therefore recognized that there is still a need in the art for an inactivated influenza vaccine composition that is capable of inducing a satisfactory systemic immune response after a single intranasal administration, does not contain an adjuvant, and meets the CHMP criteria (Ref 7) with said single administration.

Said 'CHMP criteria' are defined as follows. In the CHMP (Committee for Medicinal Products for Human Use) *Note for Guidance on Harmonisation of Requirements for Influenza Vaccines*, the following serological parameters are defined to assess the immunogenicity of inactivated influenza vaccines:
- seroprotection rate, with seroprotection defined as Hemagglutination Inhibition (HI) titer≧40,
- the seroconversion rate, with seroconversion defined as a pre-vaccination HI titer<10 and a post-vaccination HI titer≧40 or a pre-vaccination Hi titer≧10 and at least a 4-fold increase in HI titer,
- the mean fold increase, which is the geometric mean of the intra-individual increases (i.e. post-vaccination HI titer/pre-vaccination HI titer).

The CHMP requirement for influenza vaccine immunogenicity is that for each of the three virus strains in the vaccine at least one of the following criteria is met:

| criterion | adults | elderly |
| --- | --- | --- |
| seroprotection rate: | >70% | >60% |
| seroconversion rate: | >40% | >30% |
| mean fold increase: | >2.5 | >2.0 |

The invention also applies to children, for whom it was shown that they respond immunologically in a comparable manner to adults (Ref 8). The invention also applies to elderly individuals. Elderly are over sixty years old.

DESCRIPTION OF THE INVENTION

Surprisingly, and in contradiction with pre-clinical rodent data and literature on human clinical experience, we have found that the immune response in humans after a single intranasal vaccination with an inactivated influenza vaccine comprising reconstituted influenza envelopes was in accordance with all three CHMP criteria for influenza vaccine efficacy for the age group of 18-60 years old. One single intranasal administration is an inoculation of the vaccine formulation via one or both nostrils without the need for a repetition of the administration of the vaccine formulation in order to meet the above-mentioned CHMP criteria for immunogenicity of an inactivated influenza vaccine. One single administration of a vaccine (via the nasal, inhalation, oral, subcutaneous or intramuscular route) in general is a vaccination schedule which does not include multiple administrations of the vaccine that are separated in time by days or weeks known in the art as priming and boosting. A formulation designed as an intranasal or inhalational administration formulation comprises a mixture of one or more active components and excipients prepared in such a way as to allow intranasal or inhalational administration. The present invention provides a way of inducing a systemic immune response (circulating immunoglobulins or antibody-producing B cells) which is in accordance with the CHMP criteria, advantageously with a single intranasal or inhalational administration of virosomal influenza vaccine. The present invention also provides a way of inducing a local or mucosal immune response, comprising an increase in secretory immunoglobulins known as IgA at the surface of mucosal membranes, advantageously with a single intranasal or inhalational administration of virosomal influenza vaccine. Induction of specific IgG and IgA responses after intranasal administration involves the activity of lymphoid tissue in the nasal cavity (Ref 12). Such tissue is known as nasal-associated lymphoid tissue (NALT), and has been shown also to be a mucosal inductive site for cellular immune responses (Ref 13). Since it is known that virosomes have the potential to induce cellular immune responses (Ref 14, 15) the present invention also provides a way of inducing specific cytotoxic lymphocytes (CTL).

Virosomes are lipid bilayers containing viral glycoproteins. Virosomes are generally produced by extraction of membrane proteins and lipids from enveloped viruses with a detergent, followed by reconstitution of characteristic bilayers by removal of said detergent. The present invention also provides a composition of influenza virosomes comprising reconstituted influenza viral envelopes (in particular reconstituted without further addition of lipids and without the addition of an immunomodulator of immunostimulant (generally referred to as an adjuvant)) for the use of vaccination via an aerosol which is administered to the mucosa of the nasopharynx or oropharynx via one or both nostrils to achieve systemic and local immunity against influenza. A single administration via inhalation is possible also. A single oral mucosal administration is possible also.

Reconstituted influenza virosomes may be prepared from inactivated virus, which may be solubilized by a non-dialyzable detergent that is removed by adsorption to hydrophobic beads. The preparation may comprise a purified suspension of one or more influenza antigens selected from haemagglutinin (HA), neuraminidase (NA), a derivative of haemagglutinin, and a derivative of neuraminidase. The viral membrane proteins haemagglutinin and neuraminidase may be reconstituted in a membrane composed of viral lipids, containing low levels of endotoxin and ovalbumin (see Ref 9). Derivatives of haemagglutinin and/or neuraminidase are haemagglutinin and/or neuraminidase molecules with modified amino acid sequences and/or structures. Amino acids may for instance be deleted, altered or added to the sequences. Also the glycosylation patterns may be altered. The derivatives retain the ability to induce an immune response when introduced into a host.

The influenza virus used for preparing the reconstituted virosomes can be grown for instance on embryonated hens' eggs or in cell culture either on adherent cells or on cells in suspension. The virus can be for instance a wild-type or a reassortant or a genetically modified strain. The virus type can for instance be any influenza A or B subtype, including pandemic strains.

The present invention also provides vaccines. The term vaccine is understood as being directed to an immunoactive pharmaceutical preparation. In certain embodiments vaccines may comprise harmless variants or derivatives of pathogenic microorganisms that, for example, stimulate the immune system to mount defenses against the actual pathogen. In certain embodiments the vaccine, for example, induces adaptive immunity when administered to a host. A vaccine may contain a dead or attenuated form of a pathogen or a component of the pathogen, such as an antigenic component of the pathogen. The vaccine preparation may further contain a pharmaceutical carrier, which may be designed for the particular mode by which the vaccine is intended to be administered, such as a pharmaceutical carrier designed for intranasal or inhalational administration. An influenza vaccine may comprise one or more non-denatured influenza antigens, one or more of which is capable of inducing an influenza-specific immune response.

The present invention provides a composition comprising influenza virosomes comprising reconstituted envelopes of said virus, wherein the composition is designed as an intranasal or inhalational administration formulation. The invention also provides said composition in which the virosomes comprise the influenza antigens haemagglutinin and/or neuraminidase or derivatives thereof. The invention also provides said composition wherein the viral envelopes are entirely derived from viral particles. The invention also provides said composition wherein no lipid is added from an external source to the reconstituted virosomes. The invention also provides said composition wherein no separate adjuvant and/or immune stimulator is added to the composition. The invention also provides said composition wherein a single intranasal or inhalational administration of the formulation to a subject is capable of inducing a systemic immune response. The invention also provides said composition wherein the single intranasal or inhalational administration of the formulation to a subject is also capable of inducing a local immune response. The invention also provides said composition wherein the single intranasal or inhalational administration of the formulation to a subject is also capable of inducing a cytotoxic lymphocytes response. The invention also provides said composition wherein the capability of inducing a systemic immune response and/or a local immune response and/or a cytotoxic lymphocytes response is exhibited in a human being. The invention also provides said composition wherein the immune response comprises an immune response directed against the influenza antigens haemagglutinin and/or neuraminidase or derivatives thereof. In a preferred embodiment, the invention also provides said composition wherein the immune response is in accordance with the CHMP criteria for influenza vaccine. The invention also provides said composition wherein the immune response provides one or more of a seroprotection rate of >70% for adults and/or >60% for elderly, a seroconversion rate of >40% for adults and/or >30% for elderly, and a mean fold increase of >2.5 for adults and/or >2.0 for elderly. In a particularly preferred embodiment, the invention also provides said composition wherein the dose of haemagglutinin per viral strain per intranasal or inhalational administration is equal to or lower than 30 µg. Finally, the invention also provides said composition wherein the composition is a vaccine formulation comprising a pharmaceutical carrier for intranasal or inhalational administration.

The present invention further provides the use of influenza virosomes comprising reconstituted envelopes of said virus for the manufacture of a composition for intranasal or inhalational administration. The invention also provides said use in which the influenza virosomes comprise the influenza antigens haemagglutinin and/or neuraminidase or derivatives thereof. The invention also provides said use wherein the viral envelopes are entirely derived from influenza viral particles. The invention also provides said use wherein no lipid is added from an external source to the influenza virosomes in the composition. The invention also provides said use wherein no separate adjuvant and/or immune stimulator is added to the composition. The invention also provides said use wherein a single intranasal or inhalational administration of the composition to a subject is sufficient for the induction of a systemic immune response. The invention also provides said use wherein the single intranasal or inhalational administration of the composition also induces a local immune response. The invention also provides said use wherein the single intranasal or inhalational administration of the composition also induces a cytotoxic lymphocytes response. The invention also provides said use wherein the subject receiving the administration is a human being. The invention also provides said use wherein the composition induces an immune response comprising an immune response directed against the influenza antigens haemagglutinin and/or neuraminidase or derivatives thereof. In a preferred embodiment, the invention also provides said use wherein the composition induces an immune response which is in accordance with the CHMP criteria for influenza vaccine. The invention also provides said use wherein the immune response provides one or more of a seroprotection rate of >70% for adults and/or >60% for elderly, a seroconversion rate of >40% for adults and/or >30% for elderly, and a mean fold increase of >2.5 for adults and/or >2.0 for elderly. In a particularly preferred embodiment, the invention also provides said use wherein the administered dose of haemagglutinin per viral strain per intranasal or inhalational administration is equal to or lower than 30 µg. Finally, the invention also provides said use wherein the manufactured composition is a vaccine formulation.

Thus, in an embodiment the present invention provides a composition of influenza virosomes comprising reconstituted envelopes of said virus, wherein the viral envelopes are entirely derived from influenza viral particles, wherein no lipid is added from an external source to the reconstituted virosomes, wherein the virosomes comprise the influenza antigens haemagglutinin and/or neuraminidase or derivatives thereof, wherein no separate adjuvant and/or immune stimulator is added to the composition, and wherein the composition is designed as an intranasal or inhalational administration formulation, which composition is characterized in that a single intranasal or inhalational administration of said formulation to a human being is capable of inducing a systemic and/or local immune response against said influenza antigens, which systemic response is in accordance with the CHMP criteria for influenza vaccine, and wherein the dose of haemagglutinin per viral strain per intranasal or inhalational administration is lower than or equal to 30 µg.

In accordance with another embodiment the present invention provides the use of influenza virosomes comprising reconstituted envelopes of said virus for the manufacture of a composition for intranasal or inhalational administration, wherein the viral envelopes are entirely derived from influenza viral particles, wherein no lipid is added from an external source to the reconstituted virosomes, wherein the virosomes comprise the influenza antigens haemagglutinin and/or neuraminidase or derivatives thereof, and wherein no separate adjuvant and/or immune stimulator is added to the composition, which use of said influenza virosomes for the manufacture of a composition for intranasal or inhalational administration is characterized in that a single intranasal or inhalational administration of the composition to a human being is sufficient for the induction of a systemic and/or local immune response against said influenza antigens, which response is in accordance with the CHMP criteria for influenza vaccine, and wherein the dose of haemagglutinin per viral strain per intranasal or inhalational administration is lower than or equal to 30 µg.

In accordance with another embodiment the present invention provides a vaccine formulation comprising a composition of influenza virosomes comprising reconstituted envelopes of said virus, wherein the viral envelopes are entirely derived from influenza viral particles, wherein no lipid is added from an external source to the reconstituted virosomes, wherein the virosomes comprise the influenza antigens haemagglutinin and/or neuraminidase or derivatives thereof, wherein no separate adjuvant and/or immune stimulator is added to the composition, which vaccine is characterized in that the vaccine is designed for a single intranasal or inhalational administration to a human being and wherein the dose of haemagglutinin per viral strain per single intranasal or inhalational administration is lower than or equal to 30 µg.

Advantageously, said single intranasal or inhalational administration of the formulation is capable of inducing a systemic and/or local immune response in said human being. In accordance with the present invention there also is provided a device comprising a quantity of said vaccine formulation for a single intranasal or inhalational administration.

The applied dose according to the present invention of haemagglutinin per viral strain per intranasal or inhalational administration can also be lower than or equal to 25 µg, 20 µg, 15 µg, 10 µg, or 5 µg.

LITERATURE CITED (1) Maassab H F. Adaptation and growth characteristics of influenza virus at 25° C., *Nature* 213, 612-14 (1967)
(2) Maassab H F, Bryant M L. The development of live attenuated cold-adapted influenza virus vaccine for humans. *Rev. Med. Virol.* 1999 October-December; 9(4): 237-44
(3) Keitel W, Piedra P A. Live cold-adapted, reassortant in influenza vaccines (USA). In: Textbook of Influenza. Nicholson K G, Webster R G, Hay A J (Ed), Blackwel Science Oxford, UK, 373-390 (1998)
(4) Gluck U, Gebbers J O, Gluck R, Phase 1 evaluation of intranasal virosomal influenza vaccine with and without *Escherichia coli* heat-labile toxin in adult volunteers. J Virol. September 1999; 73(9):7780-6
(5) Samdal H H, Bakke H, Oftung F, Hoist J, Haugen I L, Korsvold G E, Kristoffersen A C, Krogh G, Nord K, Rappuoli R, Berstad A K H, Haneberg B. Anon-Living Nasal Influenza Vaccine Can Induce Major Humoral and Cellular Immune Responses in Humans without the Need for Adjuvants. Human Vaccines 1:2, 85-90; March/April 2005
(6) Mutsch M, Zhou W, Rhodes P, Bopp M, Chen R T, Linder T, Spyr C, Steffen R. Use of the inactivated intranasal influenza vaccine and the risk of Bell's palsy in Switzerland. N Engl J Med. Feb. 2004 26; 350(9):896-903
(7) Note for Guidance on Harmonisation of Requirements for Influenza Vaccines. EMEA/CpMP/BWP/214/96
(8) Daubeney, P., Taylor, C. J., McGaw, J., Brown, E. M., Ghosal, S., Keeton, B. R., Palache, B., Kerstens, R. Immunogenicity and tolerability of a trivalent influenza subunit vaccine (Influvac$^R$) in high-risk children aged 6 months to 4 years. BJCP March 1997, 51(2): 87-90
(9) Stegmann, T., Morselt, H. W. M., Booy, F. P., Van Breemen, J. F. L., Scherphof, G., Wilschut, J. Functional reconstitution of influenza virus envelopes. EMBO Journal 1987, 6(9): 2651-2659
(10) Treanor J, Nolan C, O'Brien D, Burt D, Lowell G, Linden J, Fries L. Intranasal administration of a proteosome-influenza vaccine is well-tolerated and induces serum and nasal secretion influenza antibodies in healthy human subjects. Vaccine 2006; 24(3):254-62.
(11) Read R. C., Naylor S. C., Potter C. W., Bond J., Jabbal-Gill I., Fisher A., Illum L., Jennings R. Effective nasal influenza vaccine delivery using chitosan. Vaccine 2005; 23(35):4367-74
(12) Kuper C F, Koornstra P J, Hameleers D M, Biewenga J, Spit B J, Duijvestein A M, van Breda Vriesman P J, Sminia T. The role of nasopharyngeal lymphoid tissue. *Immunol. Today* 1992 13:219-24
(13) Zuercher A W, Coffin S E, Thurnheer M C, Fundova P, Cebra J J. Nasal-associated lymphoid tissue is a mucosal inductive site for virus-specific humoral and cellular immune responses. *J. Immunol.* 2002 168:1796-803

(14) Huckriede A, Bungener L, Stegmann T, Daemen T, Medema J, Palache A M, Wilschut J. The virosome concept for influenza vaccines. *Vaccine* 2005 23(Suppl 1):S26-38

(15) Glück R, Burri K G, Metcalfe I. Adjuvant and antigen delivery properties of virosomes. *Curr. Drug Deliv.* 2005 2:395-400

EXAMPLES

Example 1

LPP-Virosomal Vaccine in 8-Week-Old Balb/c Mice; Intranasal Comparison of Various HA/LPP Ratios at Suboptimal HA Dose Levels Groups of 10 influenza seronegative female Balb/c mice received LPP (lipopeptide)—virosomal vaccine by intranasal administration, at HA/LPP ratios of 1:1.5, 1:0.7, 1:0.4, 1:0 (i.e. no LPP) and with 2 μg HA per dose. In addition, a control group of 10 female mice received 0 μg HA/dose (intranasal administration of vehicle).

Four preparations of LPP-containing virosomes were prepared. Briefly, inactivated influenza virus in a 30-40% sucrose solution was sedimented by centrifugation. The virus was resuspended and solubilized in a buffer containing the detergent octaethylene glycol monododecyl ether (OEG). Subsequently, viral nucleocapsid was removed by ultracentrifugation. The OEG-containing supernatant was split in 4 equal volumes and different amounts of the lipopeptide P3CSK4 in OEG-containing buffer were added (P3CSK4: N-palmitoyl-S-[2,3-bis(palmitoyloxy)-(2RS)-propyl]-[R]-cysteinyl-[S]-seryl-[S]-lysyl-[S]-lysyl-[S]-lysyl-[S]-lysine). The volume was adjusted with OEG-containing buffer. OEG was removed by adsorption to a hydrophobic resin. This resulted in the formation of LPP-containing virosomes, reconstituted viral vesicles containing HA and NA in their membranes and (optionally) LPP in their membranes. After OEG removal the virosomes were filtered through a PVDF membrane with a pore size of 0.22 μm.

The starting material was 20 mg of HA from influenza A/Wyoming/3/2003 X-147 (A/Fujian/411/200 (H3N2)-like strain), containing 252 I.U. endotoxin/100 μg HA. After solubilization 4 batches were prepared as outlined in Table 1.

TABLE 1

Preparation of virosomes

| Batch | Amount of HA as starting material (mg) | Amount of P3CSK4 added (mg) | HA/LPP Ratio |
|---|---|---|---|
| VIR-2004-11 | 5 | 7.5 | 1:1.5 |
| VIR-2004-12 | 5 | 3.5 | 1:0.7 |
| VIR-2004-13 | 5 | 2.0 | 1:0.4 |
| VIR-2004-14 | 5 | 0 | 1:0 |

The vehicle was composed of 5 mM Hepes, 145 mM NaCl, 1 mM EDTA (pH 7.4). For group E (see Table 2) vehicle was filtered through a PVDF membrane with a pore size of 0.22 μm. The 4 batches of virosomes prepared were diluted to a concentration of 200 μg/ml for intranasal and 67 μg/ml for intramuscular immunization, and aliquoted in 1-ml vials (2 per group) as indicated in Table 2. These groups of vaccines were used as outlined in Table 4.

TABLE 2

Preparation of vaccines

| Group no. | Preparation |
|---|---|
| A | VIR-2004-11 |
| B | VIR-2004-12 |
| C | VIR-2004-13 |
| D | VIR-2004-14 |
| E | Vehicle* |

*Vehicle: 5 mM Hepes, 145 mM NaCl, 1 mM EDTA (pH 7.4), filtered through a PVDF membrane with a pore size of 0.22 μm.

Analysis of Formulation

The formulations used for this study were analyzed for several variables as indicated in Table 3.

TABLE 3

Analytical data on the virosomes used for preparation of the vaccines

| Analyte | VIR-2004-11 | VIR-2004-12 | VIR-2004-13 | VIR-2004-14 |
|---|---|---|---|---|
| Protein (mg/ml)[a] | 1.7 | 1.6 | 1.5 | 1.4 |
| HA (μg/ml)[b] | 776 | 759 | 697 | 757 |
| Phospholipid (mmol/l)[c] | 0.658 | 0.692 | 0.658 | 0.682 |
| Endotoxin (I.U. per 100 μg HA)[d] | 3.1 | 1.5 | 1.9 | 1.0 |
| Ovalbumin (μg per 100 μg HA)[e] | 0.047 | 0.050 | 0.055 | 0.050 |
| Purity[f] | Mainly HA | Mainly HA | Mainly HA | Mainly HA |

[a]Lowry assay, principle: Proteins form a blue colour after treatment with alkaline copper sulphate and Folin-ciocalteu phenol reagent. The protein content is determined from the absorbance at 750 nm, using albumin BSA standard as reference. Lowry, OH, NJ Rosebrough, AL Farr, and RJ Randall. J. Biol. Chem. 193: 265. 1951. Oostra, GM, NS Mathewson, and GN Catravas. Anal. Biochem. 89: 31. 1978. Stoscheck, CM. Quantitation of Protein. Methods in Enzymology 182: 50-69 (1990). Hartree, EF. Anal Biochem 48: 422-427 (1972).
[b]PhEur: monograph 2053 and section 2.7.1
[c]Principle: Each phospholipid contains a single phosphor atom, which can be used for the quantification of the phospholipids. The phospholipids are destructed by perchloric acid and the phosphate generated is complexed by molybdate that is reduced by ascorbic acid to yield a blue colored product. The color is determined with a spectrophotometer at 812 nm. The amount of phospholipid in a sample is quantified by including a phosphate calibrator. Ames BN. Assay of inorganic phosphate, total phosphate and phosphatases. Meth. Enzymol. 1966; 8: 115-118 Böttcher CJF, van Gent CM & Pries C. A rapid and sensitive sub-micro phosphorus determination. Anal. Chim. Acta 1961; 24: 203-204
[d]Ph. Eur. 2.6.14
[e]The Ovalbumine ELISA is a direct sandwich enzyme immunoassay using immobilized polyclonalanti-ovalbumin antibodies for capture and anti ovalbumine-HRP conjugate as detection system. Conjugate and samples are incubated simultaneously. Non bound components are removed by a washing step. Substrate (TMB and $H_2O_2$) is added to the wells. The presence of specifically bound conjugate in the wells is indicated by the development of a blue color. Sulphoric acid is added to the substrate to stop the reaction, and which results in a colour change in the product to yellow. Absorbances (OD) are read at 450 nm. For optimal results a reference filter at 620 nm is used. A standard curve is created from the response of ovalbumine standards (0.3-20.0 ng/ml) included in the assay. The concentrations of the unknown samples can be interpolated from the standard curve.
[f]According to monograph 0869 and 2053: The purity of the monovalent pooled harvest is examined by polyacrylamide gel electrophoresis. Electrophoresis: according Ph. Eur 2.2.31.

Test System

Test Animals

Seven groups of ten female Balb/c mice (BALB/cAnNCrl) each were used.

At the initiation of treatment, the mice were 8-9 weeks old and weighed 17-19 g.

Animals were vaccinated intranasally on day 0, and day 14 with monovalent LPP virosomal influenza vaccine (A/Wyoming) and necropsied 21 days after the second vaccination.

Intranasal: test substances were inoculated intranasally (10 μl divided over both nostrils) under light Isoflurane/$O_2$/$N_2O$ anaesthesia with the animal in dorsal position.

TABLE 4

Treatment schedule

| Group no. | Route of administration | Vaccine formulation | No. of females | Animal No. |
|---|---|---|---|---|
| A | Intranasal | 2 μg HA, HA/LPP ratio 1:1.5 | 10 | 01-10 |
| B | Intranasal | 2 μg HA, HA/LPP ratio 1:0.7 | 10 | 11-20 |
| C | Intranasal | 2 μg HA, HA/LPP ratio 1:0.4 | 10 | 21-30 |
| D | Intranasal | 2 μg HA, HA/LPP ratio 1:0 | 10 | 31-40 |
| E | Intranasal | 2 μg HA, HA/LPP ratio 0:0 | 10 | 41-50 |

Prior to the first vaccination and 14 days after the first vaccination, orbital blood samples were collected under Isoflurane/$O_2$/$N_2$O anaesthesia. On day 35, the animals were sacrificed and blood samples were collected (exsanguinations under $O_2$/$CO_2$ anesthesia via the abdominal aorta or cardiac puncture). Serum from all samples was harvested, deep frozen, and stored in polypropylene tubes at ←10° C. until processing.

Influenza virus agglutinates red blood cells (RBCs), which is blocked in the presence of sufficient specific antibody to the virus. This phenomenon provides the basis for the hemagglutination inhibition (HI) assay, which is used to detect and quantify specific antiviral antibodies in serum. Sera were added to influenza virus and turkey RBCs. Several dilutions were tested (titration). The HI titer is defined as the reciprocal of the highest dilution that still inhibits hemagglutination. Geometrical Mean Titers (GMT) were calculated as follows:

1) calculate individual log (titer)s as the arithmetic mean of the two duplicates: [log($titer_1$)+[log($titer_2$)]/2
2) calculate the arithmetic mean of the individual log (titer)s
3) $GMT_{(group)}$=10 EXP (group mean log (titer)s)

Statistics

HI titers were summarized by vaccination group and day, using geometric mean titers. Log-transformed day 35 HI titers of the groups were analyzed by means of linear regression, to investigate the dose-response relationship between the amount of LPP in the vaccine and the GMTs.

Results
Hi Titer Analysis
GMTs are shown in Table 5.

TABLE 5

Geometric mean titers

| Group | Route of administration | HA/LPP ratio | Day 0 | Day 14 | Day 35 |
|---|---|---|---|---|---|
| A | Intranasal | 1:1.5 | 5 | 8 | 415 |
| B | Intranasal | 1:0.7 | 5 | 6 | 161 |
| C | Intranasal | 1:0.4 | 5 | 7 | 97 |
| D | Intranasal | 1:0 | 5 | 7 | 12 |
| E | Intranasal | 0:0 | 5 | 5 | 5 |

On day 0, no HA-specific antibodies could be detected in the mice (i.e. all HI titers<10). On day 14, no HA-specific antibodies could be detected in most of the mice vaccinated by the intranasal route (i.n.). All HI titers were ≦10, except for one mouse in group A (HI titer: 80), one mouse in group C (HI titer: 35) and one mouse in group D (HI titer: 160).

On day 35 a dose-response in generation of HA-specific antibodies was observed, i.e. the addition of more LPP to the vaccine led to higher antibody titers.

The (log-transformed) day 35 HI titers were compared between the groups by means of linear regression. The fitted regression slope was highly significant (P<0.0001). Thus, the observed dose-response relationship between the amount of LPP in the vaccine and the GMTs was statistically significant.

Conclusion:

Repeated intranasal vaccination of mice with the non-adjuvanted reconstituted influenza virosomes did not induce a measurable systemic immune response. Repeated intranasal vaccination using LPP adjuvanted reconstituted influenza virosomes at the same HA dose level (2 μg HA/dose) and with a rising dose of LPP showed a systemic immune response in an LPP-dose depended fashion. In sharp contrast to the present invention (see Example 2 below), these data were previously considered supportive for the consensus opinion in the art that the use of an immunostimulant (in this case LPP) is essential for intranasal vaccination with inactivated influenza vaccine, even if the influenza antigen (HA) is presented in a reconstituted virosome.

Example 2

A Double Blind, Randomized, Parallel Group Study to Investigate the Safety of the Lipopeptide Adjuvant and its Effect on the Efficacy of a Virosomal Subunit Influenza Vaccine After Nasal Delivery in Healthy Young Adults Aged ≧18 and ≦40 Years Healthy human volunteers were intranasally vaccinated with LPP (lipopeptide) adjuvanted reconstituted influenza virosomes at a dose volume of 0.2 ml (0.1 ml per nostril) containing 150 mcg HA/mL per strain and 315 mcg LPP/mL. A similar group was intranasally vaccinated with reconstituted influenza virosomes without LPP at a dose volume of 0.2 ml (0.1 ml per nostril) containing 150 mcg HA/mL per strain. The objective of the study was to confirm in man the proof of concept as was shown in mice that to obtain a satisfactory systemic immune response after intranasal vaccination with an inactivated influenza vaccine the use of an adjuvant (e.g. LPP) is required.

Study Design:

This was a double-blind, randomized parallel group study in healthy young subjects aged ≧18 and ≦40 years. The study was performed in one study center: Swiss Pharma Contract Ltd., Basel, Switzerland. The principle investigator was Dr. M. Seiberling. The study had two parts. In Part I the safety of the LPP adjuvanted virosomal subunit influenza vaccine was assessed in 12 subjects. Nine subjects were vaccinated with LPP-RVM (LPP-Reconstituted viral membranes; Influenza vaccine-surface antigen, inactivated, virosome-, adjuvanted with LPP) and three subjects with RVM (Influenza vaccine-surface antigen, inactivated, virosome-). In Part II of the study the efficacy and safety of LPP-RVM was assessed in one hundred subjects (50 per group).

The study was performed in healthy subjects. In addition, the subjects participating in Part II of the study were not vaccinated against influenza during three years previous to the start of the study. This increases the homogeneity of the study population in Part II by minimizing the number of subjects with pre-existing antibodies against influenza.

Part I:

During 14 days prior to vaccination (Visit 1), after the subject had given informed consent, he or she was screened for in- and exclusion criteria and underwent a physical exam. At this visit a sample of nasal epithelial cells was harvested for cytology and baseline cilia activity was measured with the saccharine test.

At Visit 2 (Day 1) a 4-6 mL blood sample was taken for standard hematology analysis, a 6-10 mL blood sample was taken for standard biochemistry analysis and vital signs were assessed. After randomization the subject was vaccinated with one of the two vaccine formulations and remained at the site for the first twenty-four hours after vaccination to monitor immediate local and systemic reactions and adverse events.

Vital signs were assessed four and twenty-four hours after vaccination. In addition, after twenty-four hours two blood samples were taken for standard hematology (4-6 mL) and biochemistry (6-10 mL) analysis; a sample of nasal epithelial cells was harvested for cytology and cilia activity after vaccination was measured with the saccharine test. Subjects were given a questionnaire (Questionnaire I) to take home to assess local and systemic reactions on the following day (Day 3).

The subject had to return to the study site two days after their release: Visit 3 (Day 4). At this visit local and systemic reactions were assessed and any spontaneous adverse events that occurred between the previous and the present visit were recorded. In addition, two blood samples were taken for standard hematology (4-6 mL) and biochemistry (6-10 mL) analysis and vital signs were assessed.

The subjects returned to the study site two weeks after the first vaccination on Day 15 (Visit 4). At this visit a sample of nasal epithelial cells was harvested for cytology, cilia activity was measured with the saccharine test and adverse events that occurred between Visit 3 and Visit 4 were recorded.

Part II:

During 14 days prior to the first blood and nasal wash sampling (Visit 1), after the subject had given informed consent he or she was screened for in- and exclusion criteria and his or her health was checked by physical examination.

At Visit 2 (Day −1; this visit can be combined with Visit 1) a 6 to 10 mL blood sample was taken for baseline Hemagglutination Inhibition (HI) titer determination and blood samples were taken for standard hematology (4-6 mL) and standard biochemistry (6-10 mL) analysis. A nasal wash sample was collected for determination of the baseline nasal IgA antibody titer.

The following day, at Visit 3 (Day 1) after assessment of vital signs, the subject was randomized to be vaccinated with a single dose of one of the two formulations of the nasal influenza vaccine. Any immediate local reactions, systemic reactions and adverse events were monitored at the site during the first hour after vaccination. Thereafter, vital signs were reassessed and the subject received a questionnaire to take home to record daily local and systemic reactions for the first seven days after vaccination.

Two weeks later (Visit 4; Day 15), a 6-10 mL blood sample was taken for HI titer determination, two additional blood samples were taken for standard hematology (4-6 mL) and biochemistry (6-10 mL) analysis, a nasal wash sample was taken for nasal IgA antibody titer.

Efficacy Assessments

To assess efficacy, blood samples and nasal wash samples were collected on Day −1 (baseline) and Day 15.

Blood Samples

Six to ten mL blood was collected to determine Hemagglutination Inhibition (HI) antibody titers.[1] After blood collection and coagulation (at least 30 minutes at room temperature) sera were separated and kept frozen (−20° C.) until titration. Antibody titrations were done in duplicate. The titer assigned to a sample was the geometric mean of the two determinations. Pre- and post-vaccination sera were be titrated simultaneously.

[1]Palmer D F, Dowdle W R, Coleman M T, Schild G C. Hemagglutination Inhibition Test Advanced laboratory techniques for influenza diagnosis. U.S. Dept. Hlth. Ed. Welfare, P. H. S. Atlanta; 1975:25-62

Nasal Wash Samples

For the collection of nasal wash samples, 6 mL of prewarmed saline (37° C.) was applied under rhinoscopic control in one nostril. The subject was requested to incline his/her head at a 600 angle so that the washing fluid could flow. The collected wash was applied to the second nostril which was washed under the same conditions. To the samples a preservative solution was added ($\frac{1}{100}^{th}$ of sample volume). The preservative solution contained 10 mg/ml bovine serum albumin dissolved in 100 mM Tris-HCl buffer, pH 8. Samples were directly clarified by low-speed centrifugation (10 min at 800×g) and aliquoted (to avoid repeated thawing of the samples later on) and placed on dry ice before transfer to −80° C.

IgA levels in the nasal wash samples were determined by ELISA, and statistically analyzed with the Wilcoxon test. The influenza vaccine was used as coating antigen in 96-well plates. Non-specific binding sites were blocked by incubation with a blocking buffer. The nasal washes were applied in two-fold dilutions (twelve dilutions per sample) in blocking buffer for the absorption of the influenza specific antibodies to the antigens on the 96-well plate. The 96-well plates were washed before incubation with enzyme conjugated anti-human antibodies (horse radish peroxidase or alkaline phosphatase conjugated). The non-bound anti-human antibodies were removed by washing and the amount of influenza strain specific antibody was determined by measuring the optical density after addition of the substrate for the enzymatic reaction.

Vaccine Formulation

Two different formulations of influenza vaccine were used in this study. Both formulations contained the viral antigens as recommended by the WHO for the southern hemisphere for the year 2005[2] at a dose level of 30 mcg per strain per dose of 0.2 ml

[2]WHO. Recommended composition of influenza virus vaccines for use in the 2005 influenza season. Weekly Epidem Rec. 2004; 79:369-376

A/New Caledonia/20/99 (H1N1)-like strain

A/Wellington/1/2004 (H3N2)-like strain

B/Shanghai/361/2002-like strain

Briefly, inactivated influenza virus in a 30-40% sucrose solution was sedimented by centrifugation. The virus was resuspended and solubilized in a buffer containing the detergent octaethylene glycol monododecyl ether (OEG). Subsequently, viral nucleocapsid was removed by ultracentrifugation. The OEG-containing supernatant was adjusted with the lipopeptide P3CSK4 in OEG-containing buffer or OEG-containing buffer only in the case of LPP-free reconstituted viral membranes (P3CSK4: N-palmitoyl-S-[2,3-bis(palmitoyloxy)-(2RS)-propyl]-[R]-cysteinyl-[S]-seryl-[S]-lysyl-[S]-lysyl-[S]-lysyl-[S]-lysine). OEG was removed by adsorption to a hydrophobic resin. This resulted in the formation of LPP-containing or LPP-free reconstituted viral membranes (reconstituted viral vesicles with HA and NA in their membranes and, optionally, LPP in their membranes). After OEG removal, the virosomes were filtered through a PVDF membrane with a pore size of 0.22 μm.

For each strain of virus a separate preparation was made, either with or without LPP (Table 6). The amounts of LPP added corresponded to HA/LPP ratio's of 1:0.7 (w/w).

TABLE 6

| Preparation of virosomes | | |
|---|---|---|
| Batch | LPP | Virus strain |
| VIR-2005-09 | Present | Influenza B/Jiangsu/10/2003 |
| VIR-2005-11 | Present | Influenza A/New Caledonia/20/1999 IVR-116 reassortant |
| VIR-2005-13 | Present | Influenza A/Wellington/1/2004 IVR-139 reassortant |
| VIR-2005-10 | Absent | Influenza B/Jiangsu/10/2003 |
| VIR-2005-12 | Absent | Influenza A/New Caledonia/20/1999 IVR-116 reassortant |
| VIR-2005-14 | Absent | Influenza A/Wellington/1/2004 IVR-139 reassortant |

TABLE 7

Analysis of formulation

| Analyte | VIR-2005-09 | VIR-2005-10 | VIR-2005-11 | VIR-2005-12 | VIR-2005-13 | VIR-2005-14 |
|---|---|---|---|---|---|---|
| Protein (mg/ml)[a] | 1.51 | 1.54 | 1.86 | 1.83 | 1.37 | 1.18 |
| HA (μg/ml)[b] | 805 | 854 | 711 | 784 | 704 | 644 |
| Phospholipid (mmol/l)[c] | 0.494 | 0.563 | 0.820 | 1.03 | 0.717 | 0.695 |
| Endotoxin (I.U. per 100 μg HA)[d] | <0.4 | <0.4 | <0.4 | <0.4 | <0.4 | <0.5 |
| Ovalbumin (μg per 100 μg HA)[e] | 0.068 | 0.088 | 0.037 | 0.036 | 0.132 | 0.126 |
| Purity[f] | Mainly HA | Mainly HA | Mainly HA | Mainly HA | Mainly HA | Mainly HA |

[a] Lowry assay, principle: Proteins form a blue colour after treatment with alkaline copper sulphate and Folin-ciocalteu phenol reagent. The protein content is determined from the absorbance at 750 nm, using albumin BSA standard as reference. Lowry, OH, NJ Rosebrough, AL Farr, and RJ Randall. J. Biol. Chem. 193: 265. 1951. Oostra, GM, NS Mathewson, and GN Catravas. Anal. Biochem. 89: 31. 1978. Stoscheck, CM. Quantitation of Protein. Methods in Enzymology 182: 50-69 (1990). Hartree, EF. Anal Biochem 48: 422-427 (1972).
[b] PhEur: monograph 2053 and section 2.7.1
[c] Principle: Each phospholipid contains a single phosphor atom, which can be used for the quantification of the phospholipids. The phospholipids are destructed by perchloric acid and the phosphate generated is complexed by molybdate that is reduced by ascorbic acid to yield a blue colored product. The color is determined with a spectrophotometer at 812 nm. The amount of phospholipid in a sample is quantified by including a phosphate calibrator. Ames BN. Assay of inorganic phosphate, total phosphate and phosphatases. Meth. Enzymol. 1966; 8: 115-118 Bottcher CJF, van Gent CM & Pries C. A rapid and sensitive sub-micro phosphorus determination. Anal. Chim. Acta 1961; 24: 203-204
[d] Ph.Eur. 2.6.14
[e] The Ovalbumine ELISA is a direct sandwich enzyme immunoassay using immobilized polyclonal anti-ovalbumin antibodies for capture and anti-ovalbumine-HRP conjugate as detection system. Conjugate and samples are incubated simultaneously. Non bound components are removed by a washing step. Substrate (TMB and $H_2O_2$) is added to the wells. The presence of specifically bound conjugate in the wells is indicated by the development of a blue color. Sulphoric acid is added to the substrate to For optimal results a reference filter at 620 nm is used. A standard curve is created from the response of ovalbumine standards (0.3-20.0 ng/ml) included in the assay. The concentrations of the unknown samples can be interpolated from the standard curve.
[f] According to monograph 0869 and 2053: The purity of the monovalent pooled harvest is examined by polyacrylamide gel electrophoresis. Electrophoresis: according Ph.Eur 2.2.31

Efficacy

Per viral strain, log-transformed HI antibody titers Day 15 and nasal IgA antibody titers at Day 15 were compared between the two vaccination groups by means of Wilcoxon's rank-sum test, at the two-sided significance level 0.05.

HI antibody titers at Day 15 were also analyzed by calculating the following three parameters per viral strain and per vaccination group:

the seroprotection rate, with seroprotection defined as a HI titer≧40 the seroconversion rate, with seroconversion defined as a pre-vaccination HI titer<10 and a post-vaccination HI titer≧40 or a pre-vaccination HI titer≧10 and a post-vaccination rise in HI titer of at least 4-fold the mean fold increase, i.e. the geometric mean of the fold increases in HI titer.

The efficacy data were analyzed both according to the per-protocol and the intent-to-treat principle. However, given that this was a so-called proof-of-principle study, the per-protocol analysis was considered the primary one. The intent-to-treat sample was constituted by the vaccinated subjects with some post-vaccination efficacy data. The per-protocol sample was constituted by the vaccinated subjects who completed the protocol and for whom no major protocol violations occurred. Major violations included (amongst others): violation of the in- or exclusion criteria and use of forbidden medication. Furthermore, subjects with a laboratory confirmed intercurrent influenza infection and subjects missing primary efficacy data were also excluded from the per-protocol sample. Whether or not a subject was to be excluded from the per-protocol sample was decided before the study database was unblinded.

Results

TABLE 8

CHMP evaluation humoral immune response after nasal vaccination with the Virosomal Influenza Vaccine (RVM)

| | | A (H3N2)-like | | A (H1N1)-like | | B-like | |
|---|---|---|---|---|---|---|---|
| Statistic | | LPP-RVM (N = 48) | RVM (N = 43) | LPP-RVM (N = 48) | RVM (N = 43) | LPP-RVM (N = 48) | RVM (N = 43) |
| Seroprotection Rates | | | | | | | |
| Post-Vaccination (Day 15) Seroprotection | | | | | | | |
| Yes | n(%) | 48 (100%) | 42 (97.7%) | 41 (85.4%) | 38 (88.4%) | 35 (72.9%) | 35 (81.4%) |
| No | n(%) | 0 | 1 (2.3%) | 7 (14.6%) | 5 (11.6%) | 13 (27.1%) | 8 (18.6%) |
| Total | n | 48 | 43 | 48 | 43 | 48 | 43 |
| Seroconversion Rates | | | | | | | |
| Post-Vaccination (Day 15) Seroconversion | | | | | | | |
| Yes | n(%) | 37 (77.1%) | 25 (58.1%) | 25 (52.1%) | 33 (76.7%) | 24 (50.0%) | 22 (51.2%) |
| No | n(%) | 11 (22.9%) | 18 (41.9%) | 23 (47.9%) | 10 (23.3%) | 24 (50.0%) | 21 (48.8%) |
| Total | n | 48 | 43 | 48 | 43 | 48 | 43 |

TABLE 8-continued

CHMP evaluation humoral immune response after nasal vaccination with the Virosomal Influenza Vaccine (RVM)

| Statistic | A (H3N2)-like | | A (H1N1)-like | | B-like | |
|---|---|---|---|---|---|---|
| | LPP-RVM (N = 48) | RVM (N = 43) | LPP-RVM (N = 48) | RVM (N = 43) | LPP-RVM (N = 48) | RVM (N = 43) |
| Mean Fold Increases in HI Antibody Titer | | | | | | |
| Post-Vaccination (Day 15) Mean Fold Increase | | | | | | |
| n | 48 | 43 | 48 | 43 | 48 | 43 |
| Mean* | 12.14 | 8.52 | 4.78 | 10.07 | 3.64 | 4.51 |

Note:
*Geometric mean.
RVM: Virosomal Influenza Vaccine
LPP-RVM: Virosomal Influenza Vaccine adjuvanted with Lipopeptide

TABLE 9

IgA titers in nasal washes (GMT)

| | H3N2 | | H1N1 | | B | |
|---|---|---|---|---|---|---|
| | LPP-RVM N = 48 | RVM N = 43 | LPP-RVM N = 48 | RVM N = 43 | LPP-RVM N = 48 | RVM N = 43 |
| Day 1 | 93.88 | 96.45 | 80.93 | 85.97 | 65.84 | 55.21 |
| Day 15 | 104.51 | 126.96 | 89.16 | 96.94 | 87.93 | 102.10 |

Conclusion

Unexpectedly and in contradiction with the preclinical data obtained with the same vaccine batch (example I) and as described in WO 04/110486 and clinical data (Gluck U, Gebbers J O, Gluck R, Phase 1 evaluation of intranasal virosomal influenza vaccine with and without *Escherichia coli* heat-labile toxin in adult volunteers. J Virol. September 1999; 73(9):7780-6), a satisfactory systemic immune response in accordance with the CHMP criteria for influenza vaccines was observed in the human group vaccinated only once with the non-adjuvanted reconstituted virosomal influenza vaccine.

The invention claimed is:

1. A method of inducing an immune response against one or more influenza strains, comprising administering to a human being a single intranasal or inhalational dose of a vaccine formulation comprising a composition of influenza virosomes,
   wherein the virosomes comprise reconstituted influenza virus envelopes from one or more influenza strains,
   wherein the viral envelopes are derived entirely from influenza viral particles,
   wherein no lipid from an external source is added to the virosomes,
   wherein the virosomes comprise the influenza antigen haemagglutinin,
   wherein no separate adjuvant, immune stimulator, or adjuvant and immune stimulator is added to the composition,
   wherein the vaccine is designed for a single intranasal or inhalational administration to a human being, and
   wherein the dose of haemagglutinin per viral strain per single intranasal or inhalational administration is lower than or equal to 30 µg.

2. The method according to claim 1, wherein the single intranasal or inhalational administration of the composition induces a cytotoxic lymphocytes response.

3. The method according to claim 1, wherein the immune response is in accordance with the criteria of the Committee for Medicinal Products for Human Use (CHMP criteria) for influenza vaccine.

4. The method according to claim 3, wherein the immune response provides one or more of a seroprotection rate of >70% for adults, a seroprotection rate of >60% for elderly, a seroconversion rate of >40% for adults, a seroconversion rate of >30% for elderly, a mean fold increase of >2.5 for adults, or a mean fold increase of >2.0 for elderly against one or more influenza strains.

5. The method according to claim 1, wherein the dose of haemagglutinin per viral strain per intranasal or inhalational administration is lower than or equal to 25 µg.

6. The method according to claim 1, wherein the dose of haemagglutinin per viral strain per intranasal or inhalational administration is lower than or equal to 20 µg.

7. The method according to claim 1, wherein the dose of haemagglutinin per viral strain per intranasal or inhalational administration is lower than or equal to 15 µg.

8. The method according to claim 1, wherein the dose of haemagglutinin per viral strain per intranasal or inhalational administration is lower than or equal to 10 µg.

9. The method according to claim 1, wherein the dose of haemagglutinin per viral strain per intranasal or inhalational administration is lower than or equal to 5 µg.

10. A vaccine formulation comprising a composition of influenza virosomes,
    wherein the virosomes comprise reconstituted influenza virus envelopes from one or more influenza strains,
    wherein the viral envelopes are entirely derived from influenza viral particles,
    wherein no lipid from an external source is added to the virosomes,
    wherein the virosomes comprise the influenza antigen haemagglutinin,
    wherein no separate adjuvant, immune stimulator, or adjuvant and immune stimulator is added to the composition,
    wherein the vaccine is designed for a single intranasal or inhalational administration to a human being, and
    wherein the dose of haemagglutinin per viral strain per single intranasal or inhalational administration is lower than or equal to 30 µg.

11. The vaccine formulation according to claim 10, wherein the dose of haemagglutinin per viral strain per single intranasal or inhalational administration is lower than or equal to 25 µg.

12. The vaccine formulation according to claim 10, wherein the dose of haemagglutinin per viral strain per single intranasal or inhalational administration is lower than or equal to 20 μg.

13. The vaccine formulation according to claim 10, wherein the dose of haemagglutinin per viral strain per single intranasal or inhalational administration is lower than or equal to 15 μg.

14. The vaccine formulation according to claim 10, wherein the dose of haemagglutinin per viral strain per single intranasal or inhalational administration is lower than or equal to 10 μg.

15. The vaccine formulation according to claim 10, wherein the dose of haemagglutinin per viral strain per single intranasal or inhalational administration is lower than or equal to 5 μg.

16. The vaccine formulation according to claim 10, wherein a single intranasal or inhalational administration of the formulation produces one or more of a seroprotection rate of >70% for adults, a seroprotection rate of >60% for elderly, a seroconversion rate of >40% for adults, a seroconversion rate of >30% for elderly, a mean fold increase of >2.5 for adults, or a mean fold increase of >2.0 for elderly against one or more influenza strains.

* * * * *